United States Patent [19]

Corso et al.

[11] Patent Number: 4,727,141

[45] Date of Patent: Feb. 23, 1988

[54] PROCESS FOR PREPARING TRICHLOROMELAMINE

[75] Inventors: Giampietro Corso; Vaifro Busati, both of Spinea; Dino Dall'Acqua; Gianpietro Talamini, both of Venezia-Mestre, all of Italy

[73] Assignee: Montedipe S.p.A., Milan, Italy

[21] Appl. No.: 30,673

[22] Filed: Mar. 25, 1987

[30] Foreign Application Priority Data

Mar. 28, 1986 [IT] Italy .................. 19943 A/86

[51] Int. Cl.$^4$ ........................................... C07D 251/70
[52] U.S. Cl. ...................................................... 544/199
[58] Field of Search ......................................... 544/199

[56] References Cited

U.S. PATENT DOCUMENTS 2,472,362 6/1949 Arsem ................................ 260/583
2,828,308 3/1958 Lorenz ............................... 544/199
3,364,214 1/1968 Hamprecht et al. ................ 544/199

FOREIGN PATENT DOCUMENTS 931747 7/1963 United Kingdom .
143382 3/1965 U.S.S.R. .

Primary Examiner—John M. Ford
Attorney, Agent, or Firm—Stiefel, Gross, Kurland & Pavane

[57] ABSTRACT

A process for preparing trichloromelamine starting from chlorine and melamine, with intermediate formation of an aqueous suspension of hexachloromelamine, characterized in that hexachloromelamine is solubilized by addition of a water-immiscible solvent, the aqueous phase is separated and the hexachloromelamine solution is brought into contact, in the presence of an activator, with a number of melamine moles which is equal to or lower than the number of moles of the remaining hexachloromelamine.

6 Claims, No Drawings

PROCESS FOR PREPARING TRICHLOROMELAMINE

BACKGROUND OF THE INVENTION

The processes for preparing chloromelamines disclosed in literature (see U.S. Pat. No. 2,472,361; British Pat. No. 931,747 and USSR Pat. No. 143,382) only describe reactions in an aqueous phase between melamines and chlorine or melamines and hexachloromelamine; a major drawback resides in the difficult drying of the resulting product which retains, even after centrifugation, considerable amounts of water, which results in the formation of crumbs which are difficult to pulverize. Another serious drawback is the chemical aggressivity of the reaction medium (with HCl and HClO present), which makes it necessary to use expensive, highly corrosion resistant materials, not only in the reaction section, but also in the subsequent sections of the plant (filtering and drying). The Applicant has now developed a very simple and practical method, which fully eliminates the abovesaid drawbacks.

DISCLOSURE OF THE INVENTION

In its most general form, the invention relates to a process for preparing trichloromelamine starting from chlorine and melamine, with intermediate formation of an aqueous suspension of solid hexachloromelamine, characterized in that the hexachloromelamine so formed is solubilized by addition of a water-immiscible solvent, the aqueous phase is separated and the resulting substantially anhydrous hexachloromelamine solution is contacted, in the presence of an activator, with a number of moles of non-chlorinated melamine either equal to or lower than the number of moles of hexachloromelamine remaining.

The trichloromelamine according to the present invention is 2,4,6-trichloroamino-1,3,5-triazine of formula (I):

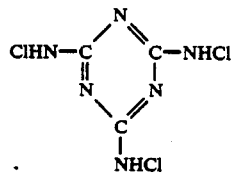

Several embodiments of the invention are possible; according to a particularly advantageous embodiment, gaseous chlorine is bubled into an aqueous suspension of melamine under stirring, the feed rate of chlorine being adjusted in such a way, that the whole chlorine amount is absorbed. The water/melamine weight ratio can range from 20 to 100 (preferably it is of about 50) and the reaction time is generally of a few tens of minutes at room temperature. The reaction can take place also by substituting a mixture containing an alkaline hypochlorite and an acid, either organic or inorganic, for chlorine.

A hexachloromelamine suspension is thus obtained, to which, always under stirring, an amount of a solvent (for example carbon tetrachloride) capable of dissolving all the hexachloromelamine is added. The aqueous phase is separated, which, if so desired, can be utilized again in the first reaction step—after removal of the hydrochloric acid—by means of neutralization, or treatment with ion-exchange resins or another equivalent technique; such re-utilization permits the recovery of the melamine fraction which has remained in solution in the aqueous phase at concentrations equal to about 0.3% by weight; subsequently, and always under stirring, melamine, in an equimolar amount or in a slightly deficient amount with respect to hexachloromelamine, is added to the hexachloromelamine solution. An activator (or promoter), for example $H_2O$ and/or acetic acid or other inorganic or organic acid, is then added, and the whole is kept under stirring, at the solvent reflux temperature, for the time required to convert hexachloromelamine (generally 1 to 6 hours); it is filtered and it is washed with the solvent to remove the hexachloromelamine residues. The residual liquids of filtration and washing can be re-used to solubilize the hexachloromelamine in subsequent processing; the solid product, after evaporation of the residual solvent, appears as a very fine white powder. The melamine conversion is usually about 90%, but it can reach also higher values if longer reaction times are employed.

The following examples are given to illustrate the invention in more detail, but they are not to be construed as a limitation of the scope of the invention.

EXAMPLE 1

Into a suspension of 21 g of melamine in 1,000 g of water, maintained under intense stirring at room temperature, there was bubbled a chlorine flow, taking care that all the chlorine should be absorbed; after 30 minutes at 20° C., a hexachloromelamine suspension with a percentage of available chlorine equal to 127% was obtained; "available chlorine" means twice the percentage-by-weight of the chlorine contained in the chlorinated melamine. Always under stirring, 1,400 g of carbon tetrachloride were added to this suspension in order to dissolve all the hexachloromelamine.

Stirring was stopped to permit the separation of the organic phase from the aqueous phase and, after removal of the latter, 14.8 g of melamine were added under stirring; the resulting suspension was brought to reflux temperature (77° C.) and after addition, by means of a proper sparger, of 4 g of water, it was refluxed for 6 hours. The product was filtered, washed with $CCl_4$ and dried in an oven at 80° C.; obtained were 43.1 g of trichloromelamine with an active chlorine content of 86.5% (corresponding to a yield of 80%).

EXAMPLE 2

Example 1 was repeated through the separation of the solution of hexachloromelamine in carbon tetrachloride; the solution was then concentrated by distillation of a portion of the solvent in order to obtain 15% by weight dissolved hexachloromelamine. 14.8 g of melamine, 1.2 g of acetic acid and 1.2 g of water were added to such solution, maintained at reflux temperature under intense stirring, whereupon it was allowed to react for 6 hours at boiling temperature; the reaction product, after filtration, washing with $CCl_4$ and drying in an oven at 80° C., appeared as a very fine white powder and consisted of trichloromelamine with 90% of available chlorine (corresponding to a yield of 90%).

What is claimed is:

1. A process for preparing trichloromelamine starting from chlorine and melamine, with intermediate formation of an aqueous suspension of solid hexachloromelamine, characterized in that the thus formed hexachloromelamine is solubilized by addition of a water-immiscible solvent, the aqueous phase is separated and the resulting substantially anhydrous solution of hexachloromelamine is brought into contact, in the presence of an activator, with a number of moles of non-chlorinated melamine equal to or lower than the number of moles of present hexachloromelamine.

2. The process according to claim 1, wherein said solvent is carbon tetrachloride, in amounts ranging from 3 to 35 kg for each kg of hexachloromelamine.

3. The process according to claim 1, wherein the hexachloromelamine solution is concentrated, by distillation of a solvent portion, before being brought into contact with the non-chlorinated melamine.

4. The process according to claim 1, wherein the residual solvent, after filtration and washing of trichloromelamine, is again utilized for solubilizing the hexachloromelamine.

5. The process according to claim 1, wherein the activator is selected from the group consisting of water, acids and mixtures thereof.

6. The process according to claim 5, wherein the activator is a mixture of water and of acetic acid in molar ratios from 1 to 10.

* * * * *